Dec. 17, 1935.
E. CHAMPNESS
Plant Pat. 161
PEACH VARIETY
Filed May 21, 1934
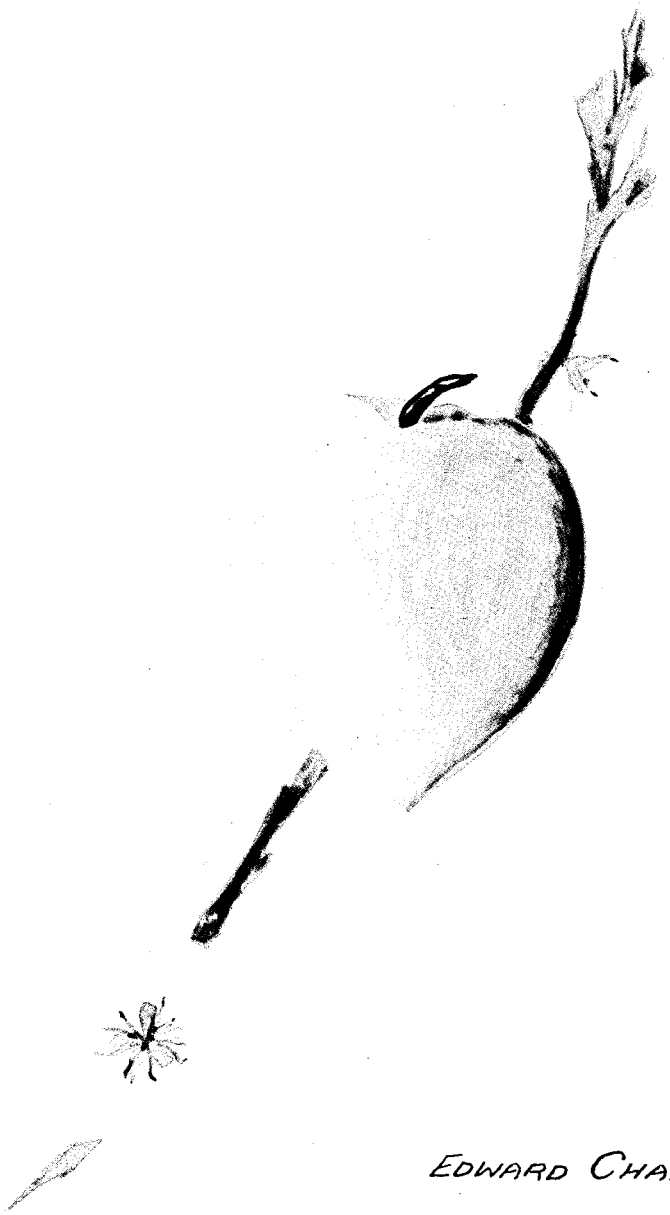
Inventor
EDWARD CHAMPNESS.,
By Marion and Fike,
Attorney Patented Dec. 17, 1935

Plant Pat. 161

UNITED STATES PATENT OFFICE

161

PEACH VARIETY

Edward Champness, Arvin, Calif., assignor to Earl Fruit Company, San Francisco, Calif., a corporation of California Application May 21, 1934, Serial No. 726,860

1 Claim. (Cl. 47—62)

My discovery has to do with a new variety of peach reproduced by budding and grafting, and characterized by certain features inherent in both Florence peaches and Quetta nectarines. My peach has never been offered for sale and a crop of the fruit was produced during the year 1933. For purposes of comparison, it may be said that the Florence peach has a pale yellow skin with a blush appearing on a cheek and extending down the suture of the peach to the point. The flesh of the Florence peach is similar to that of the white peach varieties with a slight tinge of pink appearing occasionally streaked in the flesh, with no appreciable color appearing in the flesh next to the stone. The Florence peach is a clingstone peach with exceptional fuzz on the skin. The Quetta nectarine has a skin which is dark red and glassy, with light red variations. The fruit is ordinarily about two-thirds the size of the average peach; it is a freestone variety with a smooth skin. My present peach has some of the characteristics of both of these known varieties.

As to the origin: the unit or block of trees from which the present variety matured was planted as Unit 7D Florence peaches and were purchased from some nursery the name of which is at present unknown. The first year that these trees bore a crop, it was noted that a small block of them bloomed a little later than the remainder of the planting. At the time this caused no concern due to their being young trees, however, upon time of maturity it was noted that these few trees had a peculiarly different peach than the remainder of the Florence trees in this unit. These were watched and the following year, 1933, careful attention was given to these particular trees and again they reproduced the peach herein described. The cause we believe to be due to a bud sport on the tree from which the original nursey man obtained his scion wood in making the young Florence peach trees; since that time noting the better qualities of the present peach, more trees have been made of the same type.

In the color drawing, in duplicate, accompanying this application, the fruit is shown; also a blossoming stem; certain of the blossoms of which are open and others closed or budding.

As will be seen on reference to the drawing, the peach itself is characterized by a deep pink to a light red extending all over the surface of the fruit at the time the fruit is ripe for shipment, as shown herein. However, if the fruit is left on the tree to ripen to a dead ripe stage the color increases on the surface to a dark dull red.

The flesh of my peach is characterized by considerable red coloring extending from the skin into the flesh upwards to a half inch depending on the degree of ripeness. The riper the fruit the deeper the color penetrates into the fleshy part thereof. The parts of the flesh directly in contact with the stone have a bright red color. The remaining flesh of the peach has a tinge of pink color throughout.

My peach is a semi-clingstone variety, with very little peach fuzz, and the average size is slightly larger than the average sized Florence peach.

The blossom of my peach blooms from five to seven days later than either the Florence peach or the Quetta nectarine.

The maturity seems to follow in direct ratio to the blooming defined in the foregoing paragraph.

The flavor of my peach tends strongly toward the nectarine flavor.

The shipping and carrying qualities are much better than any other early peach; the fruit remaining firm. There is very little fuzz; much less than the ordinary peach, but not quite as smooth as a nectarine.

A brief comparison of my peach with the Florence peach and the Quetta nectarine may be made as follows:—

| Florence peach | Quetta nectarine | Present peach |
|---|---|---|
| Skin—<br>Pale yellow with slight blush.<br>Clingstone with fuzzy skin. | Skin—<br>Dark glassy red with some light variation.<br>Freestone with smooth skin. | Skin—<br>Deep pink to light red.<br>Semi-cling with very little fuzz. |
| Blossom—<br>Average | Blossom—<br>Average | Blossom—<br>Different shape from either, and blooms five to seven days later, with same ratio of maturity. |
| Flavor—<br>Average | Flavor—<br>Average | Flavor—<br>Tends strongly toward Nectarine flavor. |
| Flesh—<br>Like typical white peach varieties, except tinge of light pink streaking the flesh. No color next to stone. | Flesh—<br>Red flesh, with part next to stone a dark red. | Flesh—<br>Red color extends from skin about ½ inch into the flesh depending on ripeness; remainder tinged with pink; bright red next to the stone. |

The foregoing, when taken with the color drawing, in duplicate, forming a part of this application, describes my present new variety of peach.

The following table gives further description:—

*Tree*
Medium
Vigorous
Spreading
Dense
Vase formed
Hardy
Productive
Regular bearer
*Trunk*
Medium
Medium
*Branches*
Medium
Medium
Brown
Glossy
Lenticels
Medium
Medium
*Leaves*
Medium
Medium
Oval
Lanceolate
Medium
Medium
Smooth
Finely serrate margin
Medium petiole
Glands, average

*Flower—Buds*
Hardy
Medium
Pointed
*Flower*
Late bloomer
Medium
Pink
*Fruit*
Size; larger than Florence peach
Suture; rather deep to base
Ventral surface; rounded, lipped to base
Cavity; circular
Base; cuneate
Apex; medium
Stem; medium
Skin; medium, smooth, red to pink, little or no down
Flesh; streaked with red, firm, fully colored, distinct nectarine flavor, semi-cling, red around stone, good eating qualities, firm
Stone: semi-cling, medium, ovoid, ridged
Keeping qualities; good. Shipping; good General notes: The skin is deep pink to light red all over, color increases at dead ripe stage to dark red. Smooth glossy skin, marked nectarine flavor. Flesh is bright red next to stone, and streaked with red throughout. Fruit slightly larger than Florence peach. Semi-cling. Blossoms five to seven days later than Florence peach.

Originated at Bakersfield, California in 1933.

Probably bud sport on Unit 7D Florence peaches, at ranch at Bakersfield, California.

Originated by E. Champness and first propagated in 1933, by E. Champness; none introduced to the trade as a salable commodity. Applicant is owner, and species described were grown at DiGiorgio Farms, P. O. Box 832, Bakersfield, California. Dates of first and last picking, about June 12th to 20th.

I claim:—

A peach as herein shown and described and characterized by blossoming and maturity from five to seven days later than either the Florence peach or the Quetta nectarine; and having a deep pink to light red color of the skin, semi-clingstone variety; with the flesh having a red color extending from the skin toward the stone about one-half inch depending on ripeness; a bright red color next to the stone, and a tinge of pink throughout the remainder of the flesh; with very little fuzz, and an average size slightly larger than the Florence peach; with the color of the fruit becoming deeper red as the ripeness of the fruit progresses, and blossoms differing from both the Florence peach and the Quetta nectarine.

EDWARD CHAMPNESS.